US009730606B2

United States Patent
Bianchi

(10) Patent No.: US 9,730,606 B2
(45) Date of Patent: Aug. 15, 2017

(54) SELF-REGULATED ELECTROSTIMULATION AND/OR IONTOPHORESIS DEVICE

(71) Applicant: FEELIGREEN, Grasse (FR)

(72) Inventor: Christophe Bianchi, Nice (FR)

(73) Assignee: FEELIGREEN, Grasse (FR)

( * ) Notice: Subject to any disclaimer, the term of this patent is extended or adjusted under 35 U.S.C. 154(b) by 115 days.

(21) Appl. No.: 14/760,611

(22) PCT Filed: Jan. 14, 2014

(86) PCT No.: PCT/EP2014/050531
§ 371 (c)(1),
(2) Date: Jul. 13, 2015

(87) PCT Pub. No.: WO2014/108548
PCT Pub. Date: Jul. 17, 2014

(65) Prior Publication Data
US 2015/0352356 A1 Dec. 10, 2015

(30) Foreign Application Priority Data
Jan. 14, 2013 (FR) ...................... 13 00061

(51) Int. Cl.
*A61B 5/053* (2006.01)
*A61N 1/36* (2006.01)
(Continued)

(52) U.S. Cl.
CPC .......... *A61B 5/0531* (2013.01); *A61N 1/0432* (2013.01); *A61N 1/0492* (2013.01);
(Continued)

(58) Field of Classification Search
CPC .. A61B 5/0531; A61B 5/6833; A61N 1/0432; A61N 1/36014; A61N 1/0492; A61N 1/08; A61N 1/325; A61N 1/30
(Continued)

(56) References Cited

U.S. PATENT DOCUMENTS 4,950,229 A * 8/1990 Sage, Jr. ................ A61N 1/044
604/20
5,310,403 A * 5/1994 Haynes .................... A61N 1/30
604/20
(Continued)

FOREIGN PATENT DOCUMENTS

| CN | 101869739 | 10/2010 |
| GB | 2239803 A | 7/1991 |
| GB | 2411961 A | 9/2005 |

OTHER PUBLICATIONS

Chinese Office Action for corresponding Chinese Application No. 201480004547.7, dated Jul. 20, 2016.
(Continued)

*Primary Examiner* — Manuel Mendez
(74) *Attorney, Agent, or Firm* — Hauptman Ham, LLP

(57) ABSTRACT

The invention concerns an electrostimulation and/or iontophoresis device comprising a patch (10) suitable for application to a user's skin (12) and a voltage generator (22) suitable for applying a low intensity current through the user's skin by a system of electrodes located in said patch; This device is characterized in that it comprises a self-regulator (16) that varies the voltage supplied by the voltage generator as a function of the continuous measurement of the resistivity of the user's skin beneath said patch The resistance value of the skin provided by an element for measuring the resistance of the skin (24) yields the resistivity measurement.

11 Claims, 3 Drawing Sheets

(51) Int. Cl.
  *A61N 1/04*  (2006.01)
  *A61N 1/08*  (2006.01)
  *A61N 1/30*  (2006.01)
  *A61N 1/32*  (2006.01)
  *A61B 5/00*  (2006.01)

(52) U.S. Cl.
  CPC ............... *A61N 1/08* (2013.01); *A61N 1/30* (2013.01); *A61N 1/325* (2013.01); *A61N 1/36014* (2013.01); *A61B 5/6833* (2013.01)

(58) Field of Classification Search
  USPC ............................................ 604/20; 600/582
  See application file for complete search history.

(56) References Cited

U.S. PATENT DOCUMENTS

| | | | |
|---|---|---|---|
| 5,551,953 A * | 9/1996 | Lattin | A61B 5/14514 600/582 |
| 5,823,989 A | 10/1998 | Ostrow | |
| 7,483,736 B2 * | 1/2009 | Marchitto | A61N 1/044 604/20 |
| 2003/0236487 A1 * | 12/2003 | Knowlton | A61B 18/1402 604/20 |
| 2006/0095001 A1 * | 5/2006 | Matsumura | A61N 1/0428 604/20 |
| 2007/0219480 A1 * | 9/2007 | Kamen | G05D 7/0647 604/20 |
| 2009/0043244 A1 * | 2/2009 | Inan | A61N 1/30 604/20 |
| 2012/0271206 A1 | 10/2012 | Shaleb et al. | |
| 2012/0316456 A1 | 12/2012 | Rahman et al. | |

OTHER PUBLICATIONS

International Search Report and Written Opinion for corresponding International PCT Application No. PCT/EP2014/050531, dated Mar. 20, 2014.

* cited by examiner

SELF-REGULATED ELECTROSTIMULATION AND/OR IONTOPHORESIS DEVICE

TECHNICAL FIELD

The present invention concerns methods involving subjecting dermal cells to an electrical field in order to increase their activity and/or use an electric current in order to facilitate transdermal diffusion of active substances and concerns more particularly a self-regulated electrostimulation and/or iontophoresis device.

Cell stimulation by way of an electrical field is used in many applications. Hence, the electrostimulation described in patent EP 0797421 serves to relieve pain. Electrostimulation may also be used for treatment of wrinkles, whereby the fibroblasts are subjected to an electrical field in order to increase their rate of protein production, with the proteins produced by the fibroblasts being mainly collagen and elastin, the anticipated effect of which involves improving the elasticity of the skin and hence a visible effect of reducing wrinkles. Electrostimulation may also be used for treatment of cicatrisation, for which the electrical field increases cell migration, thus facilitating cicatrisation.

Iontophoresis as described in patent EP 1727593 is a method that may be used for cosmetic and/or medical purposes in order to dispense active substances into the dermis of the skin by means of a current. The active substances contained in a reservoir or a hydrogel are generally composed of molecules of varying complexity, having high molecular masses included between 10,000 and 1,000,000 g·mol−1.

STATE OF THE ART

Application of an electric current to the surface of the skin by means of a patch for a relatively long period, as is the case in electrostimulation or iontophoresis, may result in a change in the characteristics of the skin, or even injuries ranging from superficial oedema to deep burns.

Solutions proposed in the state of the art measure at the outset of treatment physiological parameters of the skin at the patch site and data relating to the user in order to adapt the voltage delivered by the device. Injuries are still present however. Hence, there is a need to offer a device that improves the safety of such devices in order to eliminate the risks of injury while maintaining efficacy of the electrostimulation and/or iontophoresis.

SUMMARY OF THE INVENTION

Consequently, the main aim of the invention is to provide an electrostimulation and/or iontophoresis device that continuously adapts to the changes in the skin in order to avoid the user's incurring risks and particularly risks of thermal or chemical burns due to excessively high current densities.

The main aim of the invention is therefore an electrostimulation and/or iontophoresis device comprising a patch suitable for application to a user's skin and a voltage generator suitable for applying a low intensity current through the user's skin by way of a system of electrodes located in the patch. This device is characterised in that it comprises a self-regulator that varies the voltage supplied by the voltage generator as a function of the continuous measurement of the resistivity of the user's skin beneath the patch.

The applicant has noticed that continuous measurement of resistivity as a unit representing the state of the skin independent from the characteristics of the measuring device allows real-time monitoring of the current delivered and therefore a reduction in or even elimination of any risk of burns.

A second aim of the invention is an electrostimulation and/or iontophoresis device wherein the system of electrodes comprises several electrodes having a first polarity connected to one of the terminals of the voltage generator and several electrodes of the second polarity connected to the other terminal of the voltage generator, wherein said electrodes of a first polarity are arranged alternately with the electrodes of the second polarity and the electrodes at both ends of the patch have the same polarity.

A third aim of the invention is an electrostimulation and/or iontophoresis device wherein each of the electrodes, anode or cathode, comprises several contact points in order to distribute the current applied over several interfaces and therefore divide the local current density.

BRIEF DESCRIPTION OF THE DRAWINGS

The purposes, aims and characteristics of the invention will become more clearly apparent in reading the following description, made with reference to the drawings in which.

DETAILED DESCRIPTION OF THE INVENTION

Before starting on a detailed review of the embodiments of the invention, purely optional characteristics are mentioned below that may be used in combination or alternatively.

Advantageously, the present invention concerns an electrostimulation and/or iontophoresis device comprising a patch suitable for application to a user's skin and a voltage generator suitable for applying a low intensity current through the user's skin by way of a system of electrodes located in said patch, wherein said device is characterised in that it comprises a self-regulator that varies the voltage supplied by said voltage generator as a function of the continuous measurement of the resistivity of the user's skin beneath the patch; wherein said self-regulator comprises an element for measuring the resistance of the skin, with the resistance value allowing said self-regulator to calculate the resistivity value of the user's skin under said patch.

Figure 1:
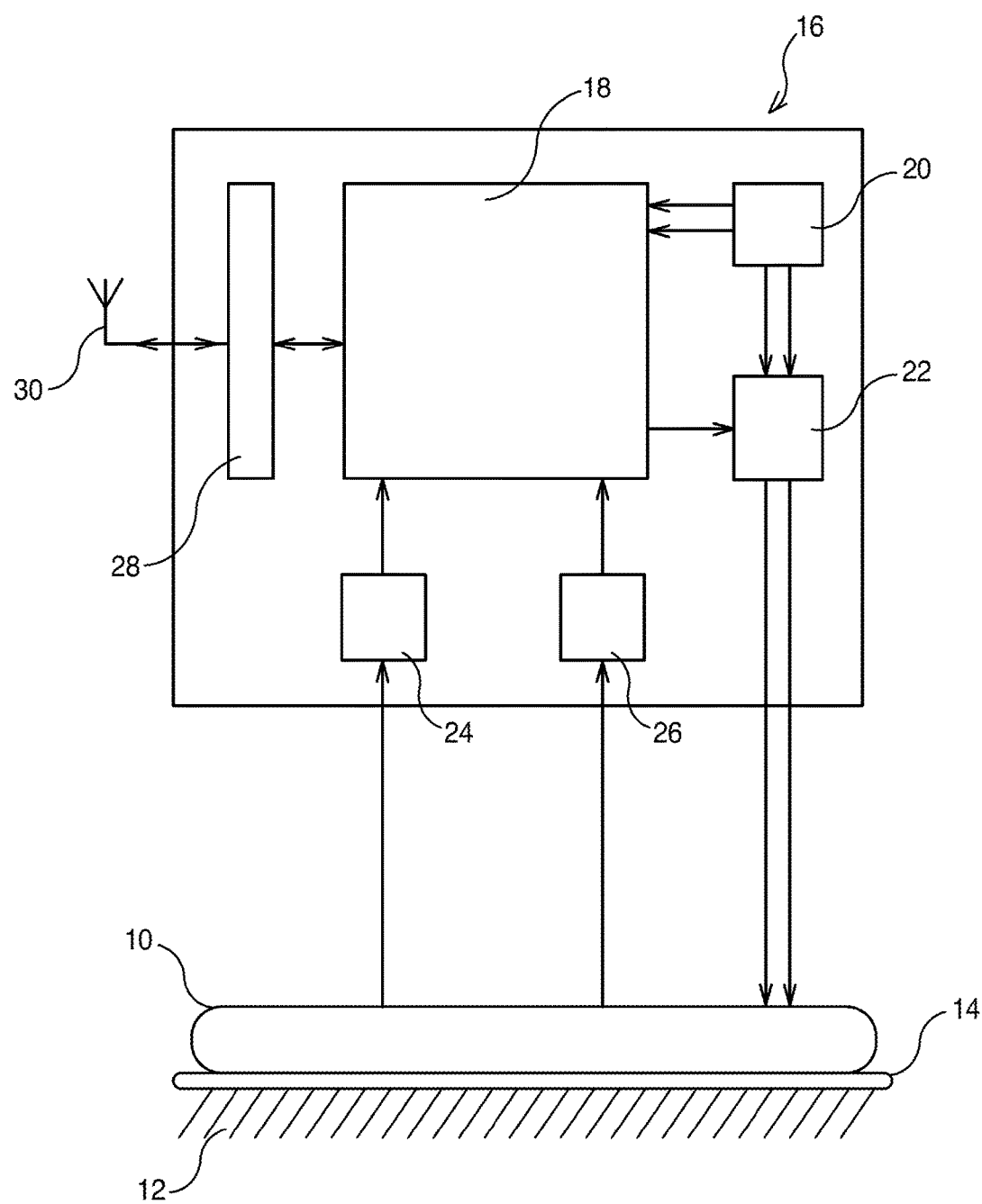
FIG. 1 is a diagrammatic representation of an iontophoresis device comprising a self-regulator according to the invention.

With reference to FIG. 1, the device according to the invention comprises a stamp 10, commonly known as a "patch", which is applied to the user's skin 12 using an adhesive product.

It should be noted that FIG. 1 represents an iontophoresis device and that in this case, the patch 10 is not applied directly to the skin, but by an intervening layer 14 instead, containing active substances as will subsequently be seen. If the device is used merely as an electrostimulation device, the patch 10 is applied directly to the user's skin.

According to the essential characteristic of the invention, the device comprises a self-regulator 16. The latter comprises a microprocessor 18 supplied by a source of electrical energy 20 such as a rechargeable storage battery or a standard battery and which controls application of a voltage to electrodes located in the patch 10 by means of a voltage generator 22.

The microprocessor 18 receives data advantageously derived from two inputs. The first input is provided by a resistance measuring element 24; the second input is provided by a temperature measuring element 26.

It should be noted that, as already mentioned above, the resistance of the skin is a measurable unit that depends on the measurement characteristics. In contrast, resistivity is a unit representing the state of the skin independent from the characteristics of the measuring device. Consequently, the measuring element 24 determines the resistance of the skin, which is easy to perform and the microprocessor 18 calculates the resistivity of the skin, the only significant value of the state of the skin, using the characteristics of the measuring element which have previously supplied to the microprocessor.

In addition to the resistivity of the skin, the temperature of the skin provided by the temperature measuring element 26 should advantageously be taken into account insofar as the voltage to be applied must also take account of this temperature. Furthermore, it is preferable for successful treatment that this temperature should not exceed a predetermined value.

Based on the resistivity value obtained, the microprocessor 18 calculates the voltage to be applied such that this voltage always remains below a threshold capable of causing injuries or burns.

The applicant has recognised resistivity as a safe and reliable parameter for monitoring the state of the skin at the patch, particularly in order to reduce the risks of injuries and/or burns. Surprisingly, resistivity is a quantity that varies as a function of the current delivered and of the skin. The variations in resistivity have proven to be rapid and wide. Measurement of resistivity in return allows determination of the voltage to be applied, which subsequently immediately follows the variations in resistivity and therefore in the current supplied. The device allows increased safety for the user without any decrease in efficacy. The current supplied is always adapted to the needs of the moment.

The device according to the invention allows continuous control of resistivity. This continuous control is particularly advantageous, as it allows permanent control of the current supplied and therefore obtain an increase in reliability and safety of the device. Continuous implies a measurement frequency of less than one second.

The present device controls the density of the current supplied, but also the penetration depth of the current.

The device according to the invention is therefore particularly reliable.

The self-regulator 16 also comprises a communication/programming interface 28 allowing the former to receive from outside the configuration to be used including the parameters to be used and communicate externally the results of the treatment applied. In the preferential embodiment, the interface 28 is connected by means of an antenna 30 to a computer, mobile telephone or other equivalent device by via a "Bluetooth" link.

It should be noted that the voltage generator 22 is capable of supplying, under the control of the microprocessor 18, either direct voltage or alternating voltage, or pulsed voltage, depending on the treatment to be applied.

A pulsed voltage is particularly advantageous, since it restricts oxidation of the electrode and thus migration of the electrode components to the skin. This transfer may indeed be particularly harmful in view of the long periods of use of this type of device.

Furthermore, the self-regulator 16 is adapted accordingly in this case in order to measure the continuous resistance of the skin, which is particularly tricky under these conditions. It is preferable to resort to microsampling. The resistivity may indeed be different at the end of a pulse and at the beginning of the next pulse. The resistivity should therefore be measured at a high frequency in order to be able to react rapidly, particularly right from the beginning of the pulse. The frequency during microsampling is greater than 1 kHz.

Figure 2:
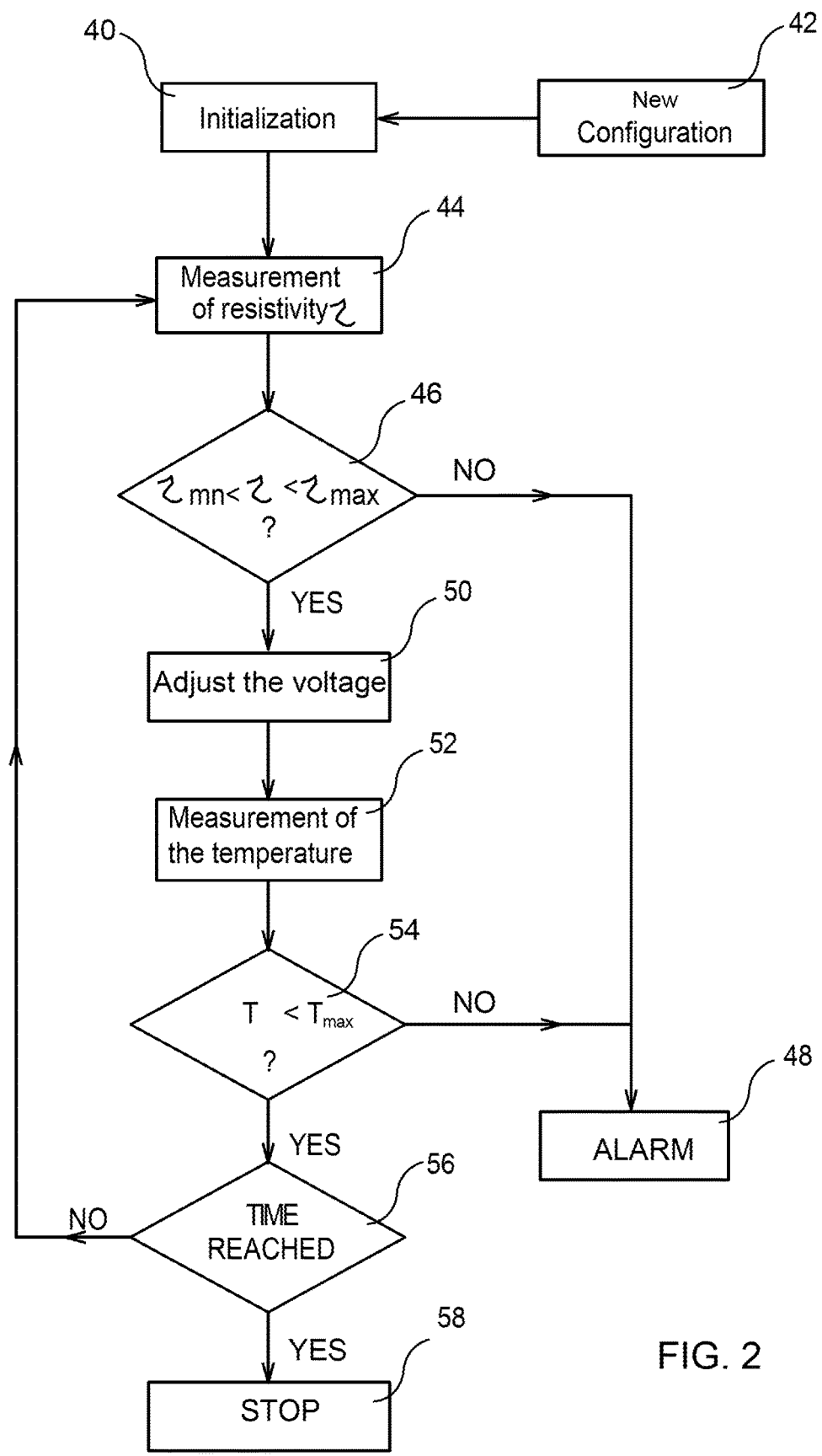
FIG. 2 is organisational flow chart of the steps executed by the self-regulator during application of a treatment by the electrostimulation and/or iontophoresis device according to the invention.

With reference to FIG. 2, which illustrates the organisational flow chart of the steps followed by the self-regulator software, the first step involves initialising the self-regulator (step 40) by imparting a new configuration to the latter (step 42) via the interface 28, which includes the characteristics of the treatment to be performed such as the voltage to be applied and the duration of treatment.

The self-regulator subsequently performs measurement of resistivity r (step 44) by means of the measuring element 24. It is subsequently determined whether the resistivity of the skin is included between a minimum value $r_{min}$ and a maximum value $r_{max}$ (step 46). Indeed, a very low resistivity value would imply that the system is short circuited and an excessively high value would mean a too high voltage, incurring risks of burns for the user.

If the resistivity value is not included between $r_{min}$ and $r_{max}$, an alarm is triggered (step 48), said alarm involving illumination of a warning light (not illustrated). If the resistivity value is included between these two values, the voltage is adjusted to the desired value (step 50).

The self-regulator subsequently measures the temperature T of the skin (step 52) by means of the measuring element 26, which allows determination of whether this temperature is less than a predetermined temperature $T_{max}$ (step 54). An excessively high skin temperature is indeed an indicator of risks of chemical burns and a temperature limitation also makes it possible to achieve additional safety in the event of long-term treatment, in order to treat bedsores for instance. An alarm is triggered (step 48) if the temperature of the skin exceeds the temperature $T_{max}$.

When the temperature of the skin does not exceed $T_{max}$, the following test involves determining whether the time allotted for the treatment has been reached (step 56). If this is not the case, the process loops back to resistivity measurement (step 44). If this is the case, the process stops (step 58).

An important parameter of the electrostimulation and/or iontophoresis device that is the subject of the invention is that the current density passing through the epidermis must be less than a predetermined density estimated at 1 mA/cm2. Indeed, if the current density applied were greater than this value, there would be risks of burns.

Consequently, according to a second subject of the invention, the device comprises several anodes and several cathodes alternating with the anodes so that the total current is divided over several anode-cathode circuits such that the current density circulating between an anode and a cathode is less than 1 mA/cm2. Furthermore, in order to prevent formation of external field lines (outside the device), the two electrodes located at both ends are of the same polarity, i.e. they are two anodes or two cathodes.

A multi-electrode device additionally offers a major advantage, i.e. the distance between an anode and a cathode must be less than a predetermined distance depending on the voltage applied. Indeed, it is important that the current lines should not penetrate into the hypodermis in order to avoid causing muscle or tendon microlesions directly or as a result of angio-ischaemia. Consequently, the distance between the anode and the cathode must be less than a predetermined distance depending on the voltage applied. Hence, for a voltage of 5 v, the distance between the anode and the cathode must be less than 2 cm.

Figure 3:
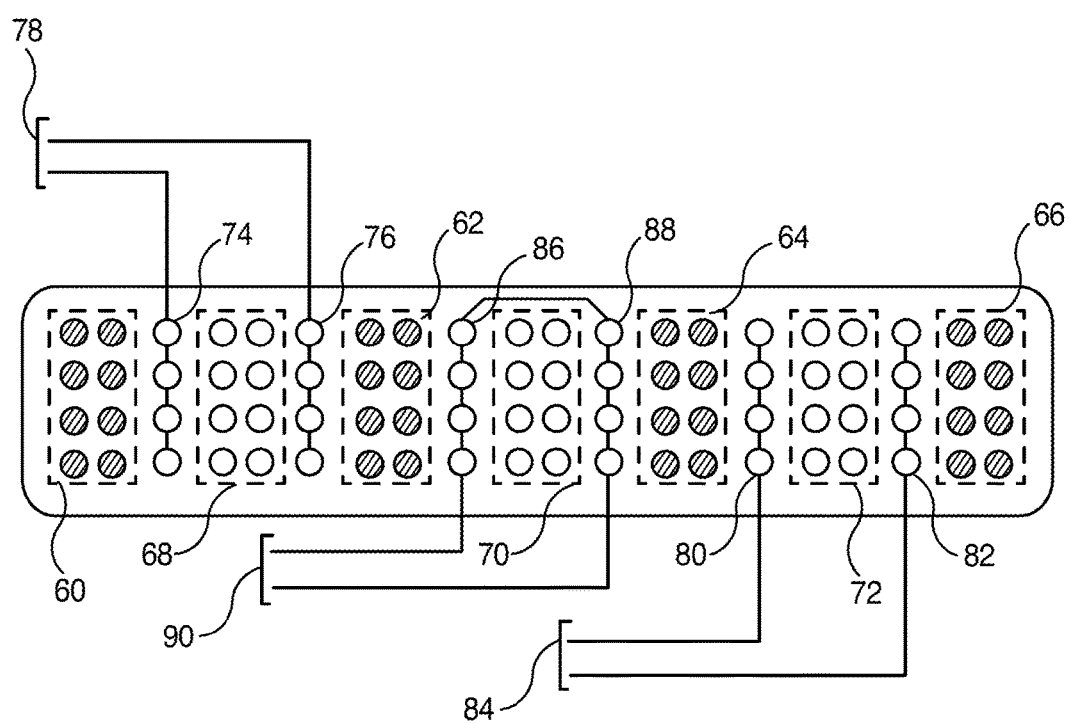
FIG. 3 represents a patch used for implementation of the electrostimulation and/or iontophoresis device according to the invention.

Thus, FIG. 3 illustrates a large-sized patch (used for example for the forehead or neck) approximately 14 cm in length, comprising 4 anodes 60, 62, 64 and 66 alternating with 3 cathodes 68, 70 and 72, wherein the 2 end electrodes of the patch are 2 anodes as mentioned above.

As mentioned above, the distance between 2 electrodes is less than or equal to a predetermined distance; 2 cm for instance for an applied voltage of 5 v.

For measuring the resistance, the device illustrated in FIG. 3 comprises sets of contact points 74 and 76 linked to the measuring element 24 by the connections 78. The contact points 74 are located midway between the anode 60 and the cathode 68 and the contact points 76 are located midway between the cathode 68 and the anode 62. It should be noted that this measurement may be performed by any appropriate means, such as a Wheatstone bridge.

In the embodiment illustrated in FIG. 3, a second set of contact points is used, i.e. the contact points 80 located midway between the anode 64 and the cathode 72 and the contact points 82 located midway between the cathode 72 and the anode 66 linked to the measuring element 26 by the connections 84, in order to obtain a mean value more representative of the resistance of the skin.

Measurement of the temperature of the skin is performed by the sets of contact points 86 and 88 linked by the connections 90 to the temperature measuring element 26. Preferentially, the sets of contact points are thermistors.

In the preferential embodiment illustrated in FIG. 3, each electrode, anode or cathode is a multipoint electrode comprising 8 contact points to ensure better distribution of the current applied through the skin. Each contact point is made of alloy or gold-nickel and has an area of 5 mm2. The value of using multipoint electrodes is derived from the fact that the epidermis of the skin is not a smooth surface and that since a single electrode has low flexibility, it is liable to become at least partially detached from the skin, thereby resulting in creation of minute electric arcs or chemical burns of the epidermis owing to an increase in the current density at the contact point.

The current intensity applied in the case of FIG. 3 is divided over 3 cathodes, each being formed of 8 contact points. Consequently, the intensity I of the current applied must comply with the inequality $I/3 \leq 8 \times 0.05$, i.e. $I \leq 1.2$ mA.

As mentioned above, if the device is used for electrostimulation, the patch directly applied to the skin serves to cause the current to penetrate into the skin in order either to stimulate the fibroblasts so as to increase their rate of collagen and elastin production, the effect of which is an improvement in the elasticity of the skin, or to treat cicatrisation.

When the device is used for iontophoresis, it comprises a layer 14 under the patch 10 containing the active substances to be dispensed into the skin, such as vitamin A or retinol (depigmenting agent), retinoic acid (acne treatment), vitamin C (antioxidant), an ion chelator such as β-alanine diacetic acid (for treatment of erythema), glycolic acid (improvement in skin texture), dexamethasone sodium phosphate (anti-inflammatory) or any other type of active substance that is ionised or presented in the form of anionic or cationic emulsions in order to be conveyed by the current.

According to a preferential embodiment, the layer 14 is a hydrogel that offers the dual advantage of not requiring any reservoir (for a liquid) and of being flexible in order to match the contour of the skin to which it is applied.

Although the device illustrated in FIG. 3 comprises the same number of contact points for each electrode, this number could of course be different without departing from the framework of the invention. Likewise, the contact points of each electrode could be arranged otherwise than in rectangular form.

The invention claimed is:

1. Electrostimulation and/or iontophoresis device comprising a patch suitable for application to a user's skin and a voltage generator suitable for applying a low intensity current through the user's skin by of a system of electrodes located in said patch;
wherein said device comprises a self-regulator that varies the voltage supplied by said voltage generator as a function of the continuous measurement of resistivity of the user's skin beneath said patch and wherein said self-regulator comprises an element for measuring resistance of the skin, the measured resistance value allowing said self-regulator to calculate resistivity value of the user's skin under said patch.

2. The device according to claim 1, wherein an alarm is triggered when the resistivity value of the skin is not between a minimum and a maximum value.

3. The device according to claim 1, wherein said self-regulator further comprises an element for measuring the temperature of the skin.

4. The device according to claim 3, wherein an alarm is triggered when the skin temperature value exceeds a maximum value.

5. The device according to claim 1, wherein said system of electrodes comprises several electrodes having a first polarity connected to one of the terminals of said voltage generator and several electrodes of a second polarity connected to the other terminal the terminals of said voltage generator, wherein said electrodes of a first polarity are arranged alternately with the electrodes of the second polarity and the electrodes at both ends of said patch have the same polarity.

6. The device according to claim 5, wherein the distance between an anode and an adjacent cathode is less than a predetermined distance of two centimeters so that the current lines do not penetrate into the hypodermis in order to avoid causing muscle or tendon microlesions.

7. The device according to claim 5, wherein each of said electrodes, anode or cathode, comprises several contact points in order to distribute the current applied over several interfaces and therefore divide the local current density.

8. The device according to claim 1, used as an iontophoresis device, comprising between said patch and the user's skin, a layer of active substances introduced with the current into the user's skin.

9. The device according to claim 8, wherein said layer of active substances is in hydrogel form.

10. A method of electrostimulation and/or iontophoresis using a device according to claim 1 comprising:
applying the patch on a user's skin;
supplying on the user's skin a pulsed voltage with the voltage generator;
continuously measuring resistance of the user's skin beneath said patch by microsampling at a frequency of less than one second;

measuring the temperature of the skin;

calculating the resistivity of the user's skin beneath said patch; and varying the voltage supplied by said voltage generator as a function of the continuous measurement of resistivity of the user's skin beneath said patch.

11. An electrostimulation and/or iontophoresis device comprising:

a patch suitable for application to a user's skin;

a voltage generator suitable for applying a low intensity current through the user's skin by of a system of electrodes located in said patch, wherein said voltage generator is capable of supplying a pulsed voltage; and a self-regulator configured to vary the voltage supplied by said voltage generator as a function of the continuous measurement of resistivity of the user's skin beneath said patch, said self-regulator comprises:

an element for measuring resistance of the skin, wherein the measured resistance value allows said self-regulator to calculate resistivity value of the user's skin under said patch, and wherein the element for measuring resistance of the skin is configured to measure resistance at a frequency of less than one second by microsampling.

* * * * *